United States Patent

Kamm et al.

[11] Patent Number: 4,627,448
[45] Date of Patent: Dec. 9, 1986

[54] TOBACCO SMOKE ARTICLE HOLDER AND METHOD THEREFOR

[76] Inventors: Roger D. Kamm, 77 Marion Rd., Watertown, Mass. 02172; Louis Fine, 601 North Grove, Oak Park, Ill. 60302

[21] Appl. No.: 705,160

[22] Filed: Feb. 25, 1985

[51] Int. Cl.⁴ .................... A24F 13/02; A24F 13/08
[52] U.S. Cl. .................................. 131/187; 131/273; 73/38
[58] Field of Search ............... 131/330, 187, 190, 273, 131/908; 73/38, 41

[56] References Cited

U.S. PATENT DOCUMENTS

| | | | |
|---|---|---|---|
| 3,115,767 | 12/1963 | Tyrrell et al. | 73/38 |
| 3,386,281 | 6/1968 | Menge et al. | 73/41 |
| 3,548,841 | 12/1970 | Caughey | 131/330 |
| 3,580,053 | 5/1971 | Molins | 73/41 |
| 4,019,366 | 4/1977 | Claflin et al. | 131/330 |
| 4,246,774 | 1/1981 | Flesselles et al. | 73/38 |

FOREIGN PATENT DOCUMENTS

| | | | |
|---|---|---|---|
| 1025173 | 2/1958 | Fed. Rep. of Germany | 73/38 |
| 1356012 | 6/1974 | United Kingdom | 73/38 |

Primary Examiner—Vincent Millin
Assistant Examiner—H. Macey
Attorney, Agent, or Firm—Charles G. Lamb

[57] ABSTRACT

A tobacco smoke article holder for a testing machine and a method of mounting a tobacco smoke article in the holder to simulate the human smoking process including an inflatably lined flow-through conduit having a depth substantially equal to the average width of a human lip and a cross-section in liner-relaxed state approximating the cross-section of the tobacco smoke article to accommodate normal insertion depth of the tobacco smoke article.

14 Claims, 2 Drawing Figures

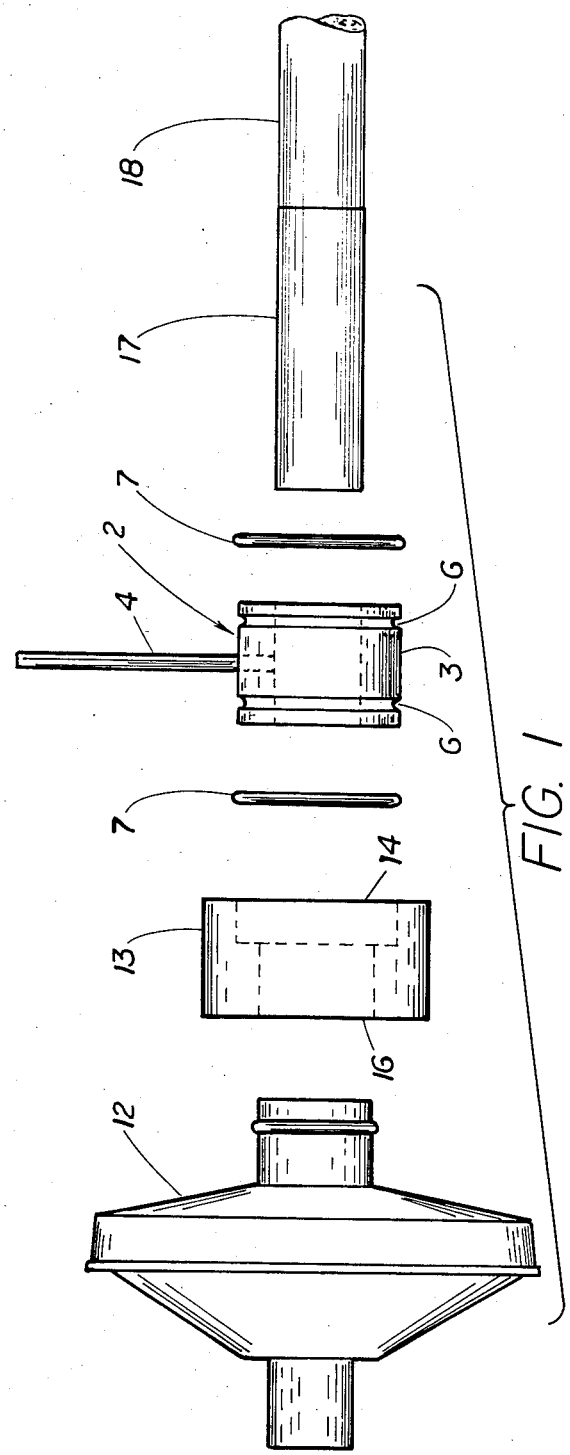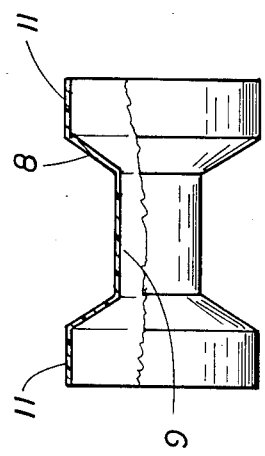

TOBACCO SMOKE ARTICLE HOLDER AND METHOD THEREFOR

BACKGROUND OF THE INVENTION

1. Field of the Invention

The present invention relates to tobacco smoke article testing and, more particularly, to an improved tobacco smoke article holder for a testing machine and a method of mounting a tobacco smoke article in the holder.

2. Description of the Prior Art

In the tobacco smoking art, it is generally well known to test smoking articles on smoking machines which collect total particulate matter on a smoke filter, the collected particulate matter being subsequently extracted from the smoke filter, measured and analyzed. It also is generally well known in the tobacco smoking art, to maintain the integrity of the mouth end of the tobacco smoke article to be tested on a testing machine without undesirable deformation which might result in an adverse effect upon testing operations and, at the same time, it is necessary to support the mouth end of a tobacco smoke article in a holder of a testing machine in sealed relationship with such holder to avoid undesirable fume and air leakage. Various tobacco smoke article holder arrangements have been utilized in the past to support the mouth ends of tobacco smoke articles in a testing machine in sealed relation therewith without mouth end deformation. Such past arrangements have included inflatable sleeves arranged to surround and seal the mouth end of a tobacco article when inflated, as disclosed in U.S. Pat. No. 3,386,281, issued to G. Menges et al, on June 4, 1968; semi-cylindrical concave jaws coated with foam rubber which compressively surround and clamp around the mouth end of a tobacco article as disclosed in U.S. Pat. No. 3,339,402, issued to W. Rudszinat on Sept. 5, 1967; and deformable elastic tubular sealing elements - the bore of which surroundingly receives the mouth end of the tobacco smoke article - as disclosed in U.S. Pat. No. 3,769,832, issued to A. Baier on Nov. 6, 1973. In fact, the broad use of fluid pressure flexible sleeves to hold article ends also is well known in non-allied arts, such as is disclosed in the machine tool chuck assembly set forth in U.S. Pat. No. 3,679,219, issued to G. N. Cameron on July 25, 1972. However, none of the abovenoted patents teaches or suggests the novel concept of applicant's present invention, which not only recognizes the importance of mouth end sealing of a tobacco smoke article in a holder of a testing machine without deformation, but further recognizes the importance of simulating human lip-mucosal relation in such tobacco smoke article holders including control of the significant parameters of human lip pressure, average lip width, mouth end insertion of the tobacco smoke article to be tested in the holder, and normal human mucosal roll - avoiding inordinate testing machine holder deformation and ventilation occlusion or impairment beyond that which might ordinarily occur with the human smoking of the tobacco article to be tested.

In addition to recognizing and providing a tobacco smoke article holder for a testing machine which best simulates human smoking to permit accurate testing, the present invention provides a novel tobacco smoke article holder assembly and method of operating the same, which is straightforward and economical in manufacture, assembly and operation, requiring a minimum of parts to assemble and a minimum of steps to efficiently and effectively operate.

Various other features of the present invention will become obvious to one skilled in the art upon reading the disclosure set forth herein.

SUMMARY OF THE INVENTION

More particularly, the present invention provides a tobacco smoke article holder for a tobacco smoke article testing machine capable of simulating tobacco smoke article filter-human lip mucosal relation comprising: a flow-through conduit having a fluid pressure inlet means passing through the wall thereof; and, an inflatable, flexible liner sized to line the inner face of the flow-through conduit with the extremities thereof fastened in sealed relation to the extremities of the conduit with the lined conduit providing an internal depth substantially equal to the average width of a human lip, the lined conduit having a cross-section when the liner of the conduit is in relaxed state approximate to the cross-section of the tobacco smoke article to be tested whereby insertion of a tobacco smoke article in one end of the conduit to a depth substantially equal to the normal insertion depth of such tobacco smoke article between the lips of a human smoker and in conformance with normal industrial testing standards results in simulating tobacco smoke article filter-human lip mucosal relation. In addition, the present invention provides a method of mounting the mouth extremity of a tobacco smoke article into a flexibly lined, fluid inflatable tobacco smoke article holder for a tobacco smoke article testing machine comprising: sizing the depth of the flexibly lined holder to a depth substantially equal to the average total width of a human lip and the cross-sectional area when in relaxed state substantially equivalent to the cross-sectional area of the mouth extremity of the tobacco smoke article; inserting the mouth extremity of the tobacco smoke article into the flexibly lined, fluid inflatable holder to a depth equivalent to the normal insertion depth of such tobacco smoke article between the lips of a human smoker; applying fluid pressure through the flexible liner on the mouth end of the tobacco smoke article equivalent to the lip pressure on the mouth end of the tobacco smoke article during normal smoking; and, selecting the appropriate elasticity for the flexible liner so as to produce the desired amount of mucosal roll behind the tobacco smoke article.

It is to be understood that various changes can be made by one skilled in the art in the arrangement, form and construction of the apparatus disclosed herein and in the several steps of the method disclosed herein without departing from the scope or spirit of the present invention.

BRIEF DESCRIPTION OF THE DRAWING

Referring to the drawing which discloses an advantageous embodiment of the inventive tobacco smoke article holder:

FIG. 1 is an exploded side view of the inventive holder flow-through conduit and a novel flow-through coupler arranged to engage with the filter holder of a testing machine; and, FIG. 2 is a side view of the inflatable liner, sized to line the inner face of the flow-through conduit of FIG. 1, with the extremities thereof sized to overlap the external grooves of the flow-through conduit of FIG. 1 and to be fastened thereto in sealed relation with the conduit.

DETAILED DESCRIPTION OF THE DRAWING

As can be seen in FIG. 1, the inventive tobacco smoke article holder, broadly referred to by reference numeral 2, includes a rigid conduit having an inlet end and an outlet end 3 which can be machined from a cast acrylic rod to have a length of approximately 12 mm. which has been found to be substantially equal to the average width of a human lip. The outer diameter of conduit 3 advantageously can be approximately 16 mm. and the internal diameter approximately 10 mm. Arranged to pass through the wall of conduit 3 intermediate the inlet end and outlet end of the conduit is a fluid pressure means in the form of a pressure tube 4 in fluid communication with the interior of the conduit which advantageously can be of 16 gauge stainless steel tubing having an outer diameter of 1.575 mm. and a length of 28.6 mm., the pressure tube being connected to a suitable controllable fluid pressure source such as an air compressor and regulator valve (not shown). It is to be noted that the other peripheral wall surface of conduit 3 is provided with a pair of spaced annular grooves 6 adjacent the inlet end and outlet end of the conduit. These grooves 6, which can each be of 1.0 mm. radius serve to receive in sealing relationship therewith, the O-ring seals 7 which, in the embodiment disclosed, can be ⅛ inch inner diameter and 1/16 inch cross-section.

Referring to FIG. 2, thin walled, flow-through liner 8 is disclosed. Liner 8 can be made from any one of a number of suitable flexible, inflatable materials known in the art and advantageously can be made from a silicone rubber shaped in cylindrical cross-section to include neck 9 between opposite ends 11.

It has been found desirable that the elastic properties of liner 8 be selected to produce an amount of mucosal roll, or lip drape, behind the tobacco smoking article equal to that observed by fiber-optic examination of normal smoking. To accomplish this, the liner 8 should have hardness properties in the range of approximately 15 to 60 Shore A, advantageously 20 to 30 Shore A, and a tensile modulus in the range of approximately 50 to approximately 200 pounds per square inch and advantageously about 80 pounds per square inch. Suitable silicone rubber materials such as those made by General Electric Company and designated SE 5218 or SE 845E have been found to be satisfactory. It is further desirable that the walls of flow-through liner 8 be relatively thin so that pressure exerted by the liner 8 on a tobacco article is substantially equal to the pressure exerted on liner 8 through pressure tube 4. It is also desirable that the shape and dimensions of linear 8 facilitate mounting without twist and without axial stretch. In the embodiment disclosed, flow-through liner 8 is 22 mm. in length with neck portion 9 being approximately 12 mm. in length equivalent to the length of conduit 3. The neck portion 9 advantageously has a liner thickness of 0.30 mm. and the opposite ends 11 a liner thickness of 0.58 mm., with the neck portion in relaxed state having a diameter of 8 mm. This diameter is equivalent to the diameter of a conventional tobacco smoke article, such as a cigarette, to be received in the cylindrical liner 8. In this regard, it is to be understood that the present invention is not limited to only conventional cigarettes or other tobacco smoke article of circular cross-section, but also can be adapted to other tobacco smoke articles such as "slims" and "ovals".

In assembling holder 2, liner 8 is inserted in the interior of the conduit to circumferentially line the inner wall surface of the conduit with the opposite ends 11 folded back to overlap the outer wall surface of conduit 3 at the conduit inlet end and outlet end and outer annular grooves 6. The O-sealing rings 7 are then slid over the liner ends overlapping the conduit inlet and outlet ends into grooves 6 of the conduit 3 to ensure an air tight seal of the conduit and liner.

Once this has been accomplished, the lined tobacco smoke article holder assembly 2 can be joined to filter holder 12 of a tobacco smoke article testing machine (not disclosed). The filter holder which can be any one of several types known in the art, such as a standard plastic Gelman holder and the testing machine, which also can be any one of several types known in the art, such as a standard Phipps & Bird, Inc. smoke testing machine, are not described in detail herein, since the testing machine per se and the filter holder do not comprise an essential part of the present invention and are known in the art.

To couple holder assembly 2 to filter holder 12, a novel coupler or collar 13 formed with a bore therethrough, which also can be machined from a cast acrylic rod, can be used. Coupler 13 is internally sized at end 14 to receive in snug sealed outer end of the lined conduit 3, the O-ring 7 at the outlet of the conduit 3 end serving to enhance the sealing relationship between coupler 13 and lined conduit 3. Opposite end 16 of coupler 13 is internally sized to engage with the extremity of filter holder 12. In the embodiment disclosed, coupler 13 can be approximately 13.6 mm. in length with an outer diameter of 22.2 mm. End 14 can have a bore diameter of 18 mm. and opposite end 16 a bore diameter of 13.9 mm.

Once the novel tobacco smoke article holder 2, including liner 8, has been assembled and joined to filter holder 12 by coupler 13, the mouth end 17 of tobacco smoke article 18, such as a cigarette, can be inserted into the relaxed liner 8 for testing. The insertion depth advantageously in 8 mm. (the current FTC standard insertion length). Fluid pressure (such as air) is applied through pressure tube 4 into the interface between the interior wall surface of the conduit 3 and liner 8 to a pressure in the range of 0 Torr to 150 Torr so that the liner 8 will exert a pressure in the range of 0 Torr to 150 Torr on the mouth end 17. Advantageously the fluid pressure is approximately 34 Torr (one Torr being considered equivalent to 1 mm. of mercury), the 34 Torr being considered the average human lip pressure on the mouth end of a cigarette, the pressures indicated being gauge pressures.

The aforedescribed thin walled flexible liner 8 of 12 mm. length with an average pressure thereon of 34 Torr best simulates human smoking with concomitant lip pressure and lip drape around the extremity of mouth end 17 of cigarette 18.

Thus, a novel tobacco smoke article holder assembly which best simulates human lip mucosal relation is provided, such holder being economical and efficient to manufacture and assemble, readily incorporable into standard testing equipment acceptable to FTC smoking procedure, creating a minimum of additional work for an operator and - most importantly - providing reliable smoke testing data.

The invention claimed is:

1. A tobacco smoke article holder for use with a tobacco article smoke testing machine capable of simulating tobacco smoke article filter - human lip mucosal relation comprising: a conduit having an inlet and an outlet end; fluid pressure means in fluid communication with the interior of the conduit; a circumferential thin-walled flexible liner sized to circumferentially line the inner wall surface of said conduit with the opposite ends of the liner at the conduit inlet end and outlet end fastened in sealed relation, with sealing means to the inlet end and outlet end of said conduit; said conduit with said liner having a length of approximately 12 mm, said lined conduit having a cross-section when said liner of said conduit is in relaxed state approximate to the cross-section of the tobacco smoke article to be tested; said circumferential flexible liner being inflated by fluid passing through said fluid pressure means into the interface of said circumferential flexible liner and inner wall surface of said conduit to a pressure in the range of 0 Torr to 150 Torr so that said liner will exert a pressure in the range of 0 Torr to 150 Torr on a tobacco smoke article inserted into the inlet end of said lined conduit resulting in simulating tobacco smoke article - human lip mucosal relation; and the sealing means at the outlet end of said lined conduit also constituting a connecting means to sealingly connecting the lined conduit to a coupler means for coupling the lined conduit to the smoke testing machine.

2. The apparatus of claim 1, said thin-walled, flexible liner comprising a thin silicone rubber tube.

3. The apparatus of claim 1, said thin-walled liner being sufficiently thin that pressure exerted on a tobacco article inserted into said liner conduit by the inflated liner, is substantially equal to the fluid pressure between said liner and the inner wall surface of said conduit.

4. The apparatus of claim 1, said fluid pressure means being positioned approximately intermediate the inlet end and outlet end of said lined conduit.

5. The apparatus of claim 1, said lined conduit having a cross-sectional area in relaxed state sized to accommodate a standard cigarette.

6. The apparatus of claim 1, said lined conduit having a circular cross-sectional area with an internal diameter when said liner is in the relaxed state of approximately 8 mm.

7. The apparatus of claim 1 wherein said means comprises a bore therethrough, the bore being sized at one end to snugly receive in sealed relationship therewith the outlet end of said lined conduit, and sized at the opposite end to snugly engage in sealed relation with a filter holder of the tobacco article testing machine.

8. The apparatus of claim 1, said flexible liner having a length before assembly to the conduit exceeding the length of said conduit, the sealing means comprising on the outer wall surface of said conduit, annular grooves adjacent the inlet and outet ends thereof; the opposite ends of said liner being folded back to overlap the annular grooves adjacent the inlet end and outlet end of said conduit; and the sealing means further comprising a pair of flexible seals engaging in said grooves to fasten and seal the opposite ends of said liner therebetween to the outer wall surface of said conduit and to permit the outlet end of said conduit to interfit in sealed relationship with said coupler connecting said conduit to the testing machine.

9. The apparatus of claim 1, said flexible liner having hardness properties in the range of approximately 15 to 60 Shore A and a tensile modulus of approximately 50 to 200 pounds per square inch.

10. The apparatus of claim 1, said flexible liner having hardness properties in the range of approximately 20 to 30 Shore A and a tensile modulus of approximately 80 pounds per square inch.

11. The apparatus of claim 1, wherein the circumferential liner is inflated to a pressure of approximately 34 Torr.

12. A cigarette article holder for a cigarette smoke testing machine capable of simulating cigarette filter - human lip mucosal relation comprising a rigid cylindrical conduit having an inlet end and an outer end and a length of approximately 12 mm; a fluid pressure tube positioned approximately intermediate the inlet and outlet ends of the conduit; a thin walled, flexible cylindrical, silicone rubber liner disposed within the conduit and overlaying the inner wall surface of said rigid conduit, said liner having a length of approximately 22 mm before assembly, the opposite ends of the liner being folded back to overlap the inlet end and outlet end of said conduit, the outer wall surface of said conduit having a pair of spaced annular grooves adjacent the inlet end and outlet end thereof; a pair of flexible O-ring seals engaging in said grooves to fasten and seal said overlapping liner ends between the O-ring seals and outer wall surface of said conduit and to interfit in sealed relation the outlet end of said lined conduit with a coupler connecting said lined conduit to the smoke testing machine; the portion of said cylindrical liner disposed within the conduit having an internal diameter when in the relaxed state of approximately 8 mm and being of 0.30 mm wall thickness to result in a pressure on the smoking article inserted into the inlet end of the lined conduit substantially equal to the pressure between said liner and said conduit when the liner is inflated by fluid entering the interface between said liner and said conduit through said fluid pressure tube.

13. A method of mounting the mouth end of a tobacco smoke article into a flexibly lined fluid inflatable tobacco smoke article conduit for a tobacco article smoke testing machine comprising the steps of: inserting the mouth end of the tobacco smoke article into the flexibly lined, fluid inflatable conduit, having a sealing means for both sealing the liner to the conduit and the conduit to a coupler coupling the conduit to the smoke testing machine, and inflating the flexibly lined, fluid inflatable tobacco smoke article conduit to a pressure whereat the flexibly lined, fluid inflatable conduit exerts a force on the mouth end of the tobacco smoke article in the range of about 0 Torr to 150 Torr throughout testing.

14. The method of claim 13, comprising the step of inflating the flexibly lined, fluid inflatable tobacco smoke article conduit to a pressure whereat the flexibly lined, fluid inflatable conduit exerts a force on the mouth end of the tobacco smoke article of about 34 Torr.

* * * * *